United States Patent [19]

Meyer et al.

[11] 4,370,487

[45] Jan. 25, 1983

[54] PROCESS FOR, RESPECTIVELY, THE PRODUCTION AND PURIFICATION OF DICARBOXYLIC AND POLYCARBOXYLIC ACID ANHYDRIDES

[76] Inventors: Gerhard Meyer, Blumenstr. 26, 8753 Obernburg; Erich Klimesch, Berlinerstr. 11, 8765 Erlenbach, both of Fed. Rep. of Germany

[21] Appl. No.: 254,384

[22] Filed: Apr. 15, 1981

[30] Foreign Application Priority Data

Apr. 25, 1980 [DE] Fed. Rep. of Germany ....... 3015988

[51] Int. Cl.$^3$ .................. C07D 307/60; C07D 493/04
[52] U.S. Cl. .................................. 549/242; 544/345; 548/430; 549/44; 549/233; 549/234; 549/235; 549/239; 549/241; 549/245; 549/247; 549/262
[58] Field of Search ............ 260/348.3, 346.7, 346.74, 260/346.76; 549/233, 234, 235, 239, 211, 242, 245, 247, 262, 44; 544/345; 548/430

[56] References Cited

U.S. PATENT DOCUMENTS

| | | | |
|---|---|---|---|
| 1,693,915 | 12/1928 | Brode et al. | 260/346.7 X |
| 1,852,782 | 4/1932 | Jaeger | 260/346.7 |
| 2,518,312 | 8/1950 | Hartig | 260/346.7 X |
| 2,985,665 | 5/1961 | Lawn et al. | 260/346.7 |
| 3,544,602 | 12/1970 | Nohe et al. | 260/346.6 |
| 3,927,039 | 12/1975 | Dehault et al. | 260/346.3 |
| 3,948,956 | 4/1976 | Handrick | 260/346.3 |

*Primary Examiner*—Richard Raymond
*Attorney, Agent, or Firm*—Michael J. Striker

[57] ABSTRACT

A method of preparation and/or purification of acid anhydrides is disclosed. Dicarboxylic or polycarboxylic acids contained in the anhydrides to be treated, are dehydrated in an organic solvent in the presence of activated carbon.

5 Claims, No Drawings

PROCESS FOR, RESPECTIVELY, THE PRODUCTION AND PURIFICATION OF DICARBOXYLIC AND POLYCARBOXYLIC ACID ANHYDRIDES

The present invention relates to a process for, respectively, the production and purification of dicarboxylic and polycarboxylic acid anhydrides. Such anhydrides are, inter alia, required in the production of epoxy and polyamide resins. In their production, these anhydrides will usually not accrue in pure form. In most instances, they will still contain products that are either not, or only incompletely anhydrated, i.e. acids still free, and furthermore also colored substances and insoluble tar-like products. Since the field of application noted above requires pure anhydrides, purification is required for anhydrides obtained by the known processes.

A number of processes has already become known for the purification of pyromellitic acid anhydride, one of the industrially most important representatives of this class of compounds. In the BE Patent No. 676 048 for instance, there is described the recrystallization of the anhydride from an aromatic hydrocarbon, with intermediate complex formation. The use of anisole as complex former is described by Jones et al. in Chem. Ind. (London), 1962, p. 1668. Recrystallization of the anhydride from dioxane or methylisobutyl-ketone is known from NL published application No. 6509701, and the vacuum sublimation of the anhydride is known from U.S. Pat. No. 2,578,326. It is, furthermore, known, how to hydrate the anhydrides into the respective acids, the former becoming dissolved in the process, and to dehydrate the acid anew, after the solution has been purified. It is furthermore known from DE published application No. 23 07 570 how to purify pyromellitic acid anhydride by multistage distillation, but this necessitates a crude product with a purity of more than 95% anhydride. It will thus be usually required that the crude product is first subjected to preliminary purification. It is, moreover, also known from DE published application No. 24 53 731, how to purify pyromellitic acid anhydride by treatment with a mono or polyalkylbenzene.

It is a disadvantage common to all the known processes, that the free carboxylic acids, present in the anhydrides in quantities that are in some instances of considerable magnitude, will become lost or can be recovered only by additional process stages and must, in given instances, be converted into anhydrides.

Unexpectedly, it was found that with the aid of activated carbon, it is possible during the course of the purification process for direct transformation into anhydrides of the carboxylic acids contained as contamination in the anhydrides. The activated carbon to be applied as per invention, is of such efficacy, that it may also be used in producing anhydrides from the respective carboxylic acids.

The object of the present invention is thus a process for, respectively, the production and purification of dicarboxylic and polycarboxylic acid anhydrides by dehydration of the respective dicarboxylic or polycarboxylic acids or, in given instances, by dehydration of the respective dicarboxylic or polycarboxylic acids contained in the anhydrides to be purified, characterized by heating at temperatures from 120° to 200° C. the dicarboxylic or polycarboxylic acid, or, respectively, the anhydride to be purified, in an organic solvent in the presence of activated carbon, and by removing the water becoming free thereby in azeotropic solution with the solvent.

The process as per invention can be taken into consideration for, respectively, the production or purification of numerous anhydrides. It is suitable for the anhydrides of cycloaliphatic, aromatic and heterocyclic dicarboxylic and polycarboxylic acids containing anhydride-forming carboxyl groups, for anhydride-forming aliphatic dicarbonylic acids such as, f.i. succinic acid and substituted succinic acids such as, f.i. alkyl-substituted succinic acids, as well as for anhydrides of aliphatic polycarboxylic acids. Apart from succinic acid, mention should be made of the following respective dicarboxylic or polycaboxylic acids which, as per invention, may be quickly and in quantities be transformed into their anhydrides:

Trimellitic acid, pyromellitic acid, dyphenyl-3.3'.4.4'-tetracarboxylic acid, diphenyl-2.2'.3.3'-tetracarboxylic acid, naphtalene-2.3.6.7-tetracarboxylic acid, 4.8-dymethyl-1.2.3.5.6.7-hexahydronaphtalene-1.2.5.6-tetracarboxylic acid, phenanthrene-2.3.9.10-tetracarboxylic acid, perylene-3.4.9.10-tetracarboxylic acid bis-(2.3-dicarboxyphenyl)-methane, bis-(3.4-dicarboxyphenyl)-methane, 1.1-bis-(2.3-dicarboxyphenyl)-ethane, 1.1-bis-(3.4-dicarboxyphenyl)-ethane, 2.2-bis-(2.3-dicarboxyphenyl)-propane, 2.3-bis-(3.4-dicarboxyphenyl)-propane, bis-(3.4-dicarboxyphenyl)-sulfone, bis-(3.4-dicarboxyphenyl)-ether, cyclopentane-1.2.3.4-tetracarboxylic acid, pyrrolidine-2.3.4.5-tetracarboxylic acid, pyrazine-2.3.5.6-tetracarboxylic acid, thiophene-2.3.4.5-tetracarboxylic acid and benzophenone-3.3'.4.4'-tetracarboxylic acid.

As reactant, use is made of an organic solvent which, under the conditions of reaction, will react neither with the acid nor with the anhydride. Selection of same is not problematic. Solvents may come into consideration in which the anhydride is soluble, as well as solvents in which the anhydride is insoluble. The former will be preferred when the anhydride to be purified contains insoluble constituents. Preference is given to the use of a solvent which is not miscible with water but which will also form an azeotrope with water, so that the separated water will be azeotropically distilled off together with the solvent; the solvent will, herein, preferentially be selected in such a manner, that its boiling point at normal pressure will be within the range of the treatment temperature as noted.

In case of using other solvents, the anhydride is separated in the usual manner, f.i. by filtration, in given instances after concentration of the reactive mixture or by extraction, etc. Separation of water from the solvent may also be effected according to known processes, f.i. by using customary drying agents such as zeolite. Preference is given to such solvents that will form a complex with the anhydride. It is of particular advantage, if the complex is soluble at treatment temperature, so that it will precipitate upon cooling and can thus be separated from water and impurities dissolved in it.

As solvents, it is particularly ethers, preferably alkylaryl-ethers, especially anisole and phenetole, aromatic and aliphatic hydrocarbons as well as chlorinated hydrocarbons, that come into consideration. Suitable ethers are, for instance, apart from anisole and phenetole, also benzylmethylether, butylisobutylether, butylphenylether, diisoamylether, butylisoamylether, phenylisopropylether, diphenylether and phenylenedimethylether. Suitable hydrocarbons are, in particular, sec. butylbenzene, tert, butylbenzene, diethylbenzene, trimethylbenzene, cumol, cymol and propylbenzene. Examples of suitable chlorinated hydrocarbons are pentachloroethane, tetrachloroethane, dichlorobenzene and chlorotoluene.

Practically all commercially available types of activated carbons may be used herein as activated carbon, such as, f.i. the pulverized decolorant carbons, granulated water purification carbons and shaped catalyst carbons. The specific surface, degrees of granulation, ash contents, metallic contents, pore volumes and other characteristic features of activated carbon are of no, or only nonessential consequence in the process as per invention. Regarding commercially available types of activated carbon, reference is made to Ullmanns Enzyklopädie der technischen Chemie, 4th edition (1977), vol. 14, p. 627, Verlag Chemie, Weinheim/New York. Pulverized activated carbon is used with preference. The quantity of activated carbon may be varied within wide limits. The catalytic efficacy of activated carbon can be distinctly recognized already at 0.5 g/100 g dicarboxylic acid, but will increase sharply with increased quantities of activated carbon. After treatment has been performed, the activated carbon may be used for subsequent preparations without purification or activation, and its activity will remain without any change, even after a number of preparations has been made. Since longer treatment times at high temperatures will cause decarboxylation and discoloration of the anhydrides, it is preferable to use a minimum of 1% by weight—relative to carboxylic acid—of activated carbon. The preferred quantity of activated carbon is 3 to 20% by weight, relative to carboxylic acid, wherein carboxylic acid is to be taken as, respectively, the carboxylic acid to undergo anhydration or the carboxylic acid contained as contamination in the anhydride.

The treatment temperature will depend upon the anhydride to be formed. As a rule, dehydration will take place in the range from 120° to 200° C., in the case of pyromellitic acid for instance between 140° to 170° C. The treatment temperature should not be essentially higher than the temperature at which dehydration, i.e. the formation of the anhydride, will ensue. This is to a good purpose not only on grounds of economy, but also because higher temperatures are conducive to discoloration and decarboxylation of the product.

The reaction times are dependent upon the acid used, the quantity of activated carbon, the reaction medium and the temperature of the reaction. As a rule, said reaction times will be of a duration between 1 to 10 hours. In purification of anhydrides, the required treatment time will, of course, also depend upon the carboxylic acid content of the anhydride.

Compared with the known processes, the process as per invention is of the advantage that the carboxylic acids are transformed in quantity into the respective anhydrides. This is of great importance in the purification of anhydrides. It has been shown that acid contaminations in anhydrides which are used in the production of polyimides, may considerably interfere with the process of polycondensation, so that no polymers are obtained that could be reproduced in respect of the molecular weight. These disadvantages have been overcome by the process as per invention. In the production of polyimides, reproducible products will at any time be yielded by anhydrides produced or purified according to the process as per invention.

The process as per invention shall be explained more closely by the examples below:

EXAMPLE 1

50.0 g crude pyromellitic acid dianhydride (PMDA), (17.5 mol equiv. $H^+/g$), 400 ml anisole and 3.0 g activated carbon purest, Merck Article No. 2184, were heated in a 1 liter three-necked flask equipped with stirrer, thermometer and water separator, heating being effected by oil bath (temp. 180°–185° C.) to the reflux temperature (152°–154° C.). Water separation was ended after 4 hours; 2.0 g water had separated. The hot solution was pressed through heated frit, the filter residue subjected to subsequent washing with 200 ml hot anisole and then dried in a vacuum drying cabinet at 50° C. It still contained, apart from the activated carbon, 1.8 g of undissolved substance. Upon cooling of the filtrate, the PMDA complex of the anisole segregated in the shape of golden-yellow needles; it was siphoned off at room temperature, washed with 50 ml anisole and decomposed in a rotary vacuum evaporator at bath temperature 80°–85° C. and 2000 PA (=20 mbar). The anisole distilled off therein, the PMDA remained in the flask as white powder; it was after-dried in a vacuum drying cabinet, (70° C., 13000 Pa=130 mbar; 12 hours), weighed and analyzed. The yield was 43.2 g PMDA which melted at 282.8° C. (Mettler melting point determinator PF51) and which, upon titration with 0.1 n NaOH, yielded an $H^+$ equivalent of 18.30/18.40 (mol equivalence per gram), (theoretical value: 18.35). A small portion of the PMDA evaporated with the anisole and condensed as complex at the cold parts of the evaporator. It was dissolved in acetone and isolated by concentration of the acetone solution. 2.0 g PMDA-anisole complex were thus obtained, corresponding to 1.35 mg PMDA. By concentration of the anisole mother liquor after separation of the complex, 2.90 g residue were obtained, (equivalent to 1.95 g PMDA).

COMPARATIVE EXAMPLE 1

In preparation and performing, this experiment corresponded fully to the one described in example 1, and only the activated carbon was omitted herein. No water separation could be noted within the experiment time of 4 hours. Undissolvable residue weighing 14.8 g remained after hot filtration. 31.7 g PMDA were obtained by decomposition of the complex obtained upon cooling of the mother liquor, and a further 0.35 g from the acetone used in rinsing the rotary evaporator.

Concentration of the mother liquor yielded 3.0 g PMDA-anisole complex as residue, equivalent to 2.0 g PMDA.

Comparison to example 1 clearly illustrates the catalytic influence of activated carbon upon anhydride formation and the improved yield concatenated therewith.

EXAMPLE 2

In this example otherwise fully analogous to example 1 in preparation and performing, activated carbon recovered from the preceding preparation by expelling of the mother liquor and not subjected to intermediate purification, was used again instead of fresh activated carbon, Merck Art. No. 2184. The rate of water separation and the separated water quantity (4 hours, 2.0 ml) were analogous to example 1, with the identical quantity and quality of products (43.2 g or, respectively, 43.4 g; F=282.8° C.; 18.35 mol equiv. $H^+/g$).

EXAMPLES 3 TO 7

In each of these experiments, 50.00 g pyromellitic acid in 400 ml anisole were boiled under the same conditions as in Example 1, and the separated water of the reaction measured at predetermined time intervals. 3.0 g of different types of activated carbon were used as respective catalyst. Water separation as measure of anhydride formation is shown in the following table.

TABLE 1

| Example No. | Addition | \multicolumn{7}{c}{separated water qu'ty (g) and (% of theory), by elapsed hours} |
|---|---|---|---|---|---|---|---|---|

| Example No. | Addition | 1 | 2 | 3 | 4 | 5 | 6 | 7 (h) |
|---|---|---|---|---|---|---|---|---|
| 3 | Activ. carb., purest, Merck, Art, No.2184 | 2,80 (39) | 3,82 (54) | 4,62 (65) | 5,24 (74) | 5,93 (84) | 6,65 (94) | 7,17 (100) |
| 4 | Supersorbon WS4 act. carb. granulated | 2,46 (35) | 2,89 (41) | 2,99 (42) | 3,05 (43) | 3,10 (44) | 3,13 (44) | 3,14 (44) |
| 5 | Supersorbon WS 4 act. carb. ground | 2,20 (31) | 3,00 (42) | 3,65 (51) | 4,45 (63) | — | 5,35 (75) | 6,00 (84) |
| 6 | Norit 5030 act. carbon, granulated | — | 0,64 (9) | — | 0,86 (12) | — | 1,04 (15) | 1,14 (16) |
| 7 | Norit 5030 act. carbon ground | 2,20 (30) | 2,60 (36) | 3,25 (45) | 3,8 (53) | 4,45 (62) | 5,05 (70) | 5,50 (76) |

EXAMPLE 8

50.0 g pyromellitic acid were boiled under reflux with 400 ml anisole and 3.0 g activated carbon, Merck Art. No. 2184, under the same conditions as in example 1 and then processed. 4.3 g (60.6% of the theory) water separated in the course of 2.5 hours. 27.3 g (=64% of the theory) pyromellitic acid anhydride were obtained and the remainder of 18.0 g, (36%) was filtered off as unchanged pyromellitic acid, together with the activated carbon.

This example shows that water separation and dianhydride formation are of rather exact commensurateness.

EXAMPLES 9 to 12 AND COMPARATIVE EXAMPLE 2

50.0 g pyromellitic acid, 400 ml anisole and varying quantities of activated carbon, Merck Art. 2184, were boiled under reflux in the apparatus described in example 1 and the separated water of the reaction measured at predetermined intervals. The quantity of active carbon was varied between 0 and 10 g. The results are shown in table 2.

TABLE 2

| Example No. | Activated carbon | \multicolumn{11}{c}{Separated water in g and % of theory (in brackets) within hours} |
|---|---|---|---|---|---|---|---|---|---|---|---|---|

| Example No. | Activated carbon | 0,5 | 1 | 1,5 | 2 | 2,5 | 3 | 3,5 | 4 | 4,5 | 5,5 | 6,5 | 7,5 [h] |
|---|---|---|---|---|---|---|---|---|---|---|---|---|---|
| Comparative example | 0 | | | | | | | | | | | | 0,7 (10) |
| 9 | 0,5 | — | 0,1 (1) | 0,2 (3) | 0,4 (5) | — | 0,6 (8) | — | 1,0 (14) | 1,2 (17) | 1,5 (21) | 1,8 (25) | 1,9 (27) |
| 10 | 3,0 | 0,5 (7) | 0,9 (13) | 1,3 (18) | 2,1 (30) | 2,6 (37) | 3,1 (44) | 3,6 (51) | 3,8 (53) | 4,3 (61) | 5,0 (70) | 5,7 (80) | 6,4 (90) |
| 11 | 5,0 | 0,8 (11) | 2,3 (32) | 3,2 (45) | 4,0 (56) | 5,0 (70) | 5,6 (79) | 6,3 (89) | 6,7 (94) | 6,9 (97) | — | — | 7,0 (99) |
| 12 | 10,0 | 2,7 (38) | 4,9 (69) | 6,5 (91) | 6,9 (97) | 7,2 (101) | | | | | | | |

The examples illustrate the influence of the activated-carbon quantity upon the rate of reaction. With only 1% addition (example 9), water separation is already increased threefold when compared to the blind experiment without activated carbon, and at 20% activated carbon (example 12), the reaction is completed after 2½ hours.

EXAMPLES 13 and 14, AND COMPARATIVE EXAMPLES 3 AND 4

50.0 g pyromellitic acid were boiled under reflux in the apparatus described in example 1, with, respectively, phenetole or diethylbenzene, with and also without the addition of 3 g activated carbon, Merck Art. No. 2184, and the separating water quantity measured at predetermined time intervals. The boiling temperatures were, respectively, 168° C. (phenetol) and 172° C. (diethylenebenzene). The water quantities separated in the respective instances are shown in table 3.

TABLE 3

| | Comparative example 3 | Example 13 | Comparative example 4 | Example 14 |
|---|---|---|---|---|
| | \multicolumn{4}{c}{Solvent} | | | |
| | \multicolumn{2}{c}{Phenetole} | \multicolumn{2}{c}{Diethylbenzene} |
| Activated carbon | — | 3,0 g | — | 3,0 g |
| Water separation in g per hours (%) | | | | |
| 0,5 h | 0,3 (4) | 1,4 (20) | 0,6 (8) | 0,7 (10) |
| 1,0 h | 0,6 (8) | 2,7 (38) | 0,9 (13) | 2,0 (28) |
| 1,5 h | 0,8 (11) | 4,2 (59) | 1,3 (18) | 2,6 (37) |
| 2,0 h | 1,1 (15) | 5,3 (75) | 1,7 (24) | 3,5 (49) |
| 2,5 h | 1,3 (18) | 6,4 (90) | 2,2 (31) | 4,4 (62) |
| 3,0 h | 1,5 (21) | 6,8 (96) | 2,6 (37) | 5,4 (76) |
| 3,5 h | — | 7,2 (101)+ | 2,9 (41) | 5,8 (82) |
| 4,0 h | 2,0 (28) | 7,3 (103)+ | 3,2 (45) | 6,1 (86) |
| 4,5 h | | | 3,5 (49) | 6,5 (92) |
| 5,5 h | | | 4,2 (59) | 7,0 (99) |
| 6,5 h | | | 5,2 (73) | 7,2 (101)+ |

+The pyromellitic acid used contained some moisture

Examples 13 and 14 prove that anhydride formation in case of phenetole and anisole will be strongly accelerated in comparison with the non-catalyzed reaction (examples 3 and 4), even though the non-catalyzed reaction will be noticeable due to the higher boiling temperature of these solvents.

EXAMPLE 15 AND COMPARATIVE EXAMPLE 5

50.0 g pyromellitic acid, 400 ml n-undecane and 3.0 g activated carbon Merck Art. No. 2184 were reacted in the apparatus described in example 1. By the application of a slight vacuum, the boiling point was lowered to the temperature shown in the following table 4. The separating water of the reaction was measured (example 15). A parallel experiment without the addition of activated carbon was performed under identical conditions, (Comparative example 5).

Table 4 represents the results.

TABLE 4

| Addition | Example 15 activated carbon | Comparative example — |
|---|---|---|
| Water quantity in g and % at $K_p$ 280-350 = 160-167° C. in 5½ hours | 3.4 (48) | 1.3 (18) |
| $K_p$ 400 = 174° C. after a further 6 hours | 3.1 (44) | 2.0 (28) |
| total | 6.5 (92) | 3.3 (46) |

The pyromellitic acid anhydride formed therein, was insoluble in the reactive medium, also in hot state; it was siphoned off together with the activated carbon and extracted from it with acetone; 39.0 g PMDA (=91% of theory) were obtained. The activated carbon also contained 4.3 g pyromellitic acid (=8.5% of theory). Example 15 shows that activated carbon will accelerate anhydride formation in an aliphatic hydrocarbon, although water separation in this medium will ensue more slowly than in phenetole and although the reactive temperature was approximately equal in both cases.

EXAMPLE 16

50.0 g pyromellitic acid and 400 ml 1,3,5-trimethylbenzene, (Kp=176° C.) were initially boiled without activated carbon; after an initially rapid water separation caused by the water content of the acid, separation ceased. 3.0 g activated carbon, Merck, Article No. 2184 were then added and water separation determined over a period of 8 hours. (Vide table 5)

TABLE 5

| Time (hours) | 1 | 2 | 3 | 4 | 5 | 6 | 7 | 8 |
|---|---|---|---|---|---|---|---|---|
| Water separation in g and (%) | 0.7 (10) | 1.4 (20) | — | 3.6 (51) | 4.1 (58) | 4.7 (66) | 4.95 (70) | 5.15 (73) |

EXAMPLE 17 AND COMPARATIVE EXAMPLE 6

50.0 g pyromellitic acid, 400 ml o-chlorotoluene (Kp=157° C.) and 3.0 g activated carbon, Merck, Art. No. 2184, were boiled under reflux in the apparatus described in example 1. (example 17). A blind experiment, without using activated carbon, was conducted simultaneously. (Comparative example 6). Since the densities of water and o-chlorotoluene are hardly different from each other, it was impossible to separate the water from the azeotrope. Therefore, distillate had to be continually drawn off, dried with sodium sulfate and then added again to the reaction. The total reaction time amounted in both cases to 7 hours. Hot filtering was performed thereupon.

During cooling of the filtrate, a weakly yellow-colored crystalline substance (1. fraction) crystallized out of it and was separated. The activated-carbon residue was then boiled out twice, conjointly with the mother liquor after the preceding crystalline fraction had been separated and two additional crystalline substances (2 and 3) were obtained thereby. It was thus possible to isolate from the preparation containing activated carbon (example 17), 16.2 g (38%) pyromellitic dianhydride with a Fp=282.6° C. and 18.20 mol equiv. $H^+$/g. The activated carbon contained 30 g pyromellitic acid (60%).

In the preparation without activated carbon (comparative example 6), there were isolated 2.4 g. (5.6%) pyromellitic acid dianhydride of identical quality as in example 17 and 43.5 g (87%) pyromellitic acid.

EXAMPLE 18

50.0 g pyromellitic acid and 400 ml of 1-decene ($K_p$=169° C.), were boiled for 1½ hours in the apparatus described in example 1, initially without the addition of activated carbon, and with no noticeable water separation occurring therein. 3.0 g activated carbon, Merck, Art. No. 2184 were then added, and continued under reflux for 10 hours; the separating water from the reaction was measured at predetermined intervals. (Table 6)

TABLE 6

| Time (hours) | 1 | 2 | 3 | 4 | 5 | 7 | 10 |
|---|---|---|---|---|---|---|---|
| Water separation in g and (%) | 1,1 (15) | 1,7 (24) | 2,5 (35) | 3,0 (42) | 3,5 (49) | 4,4 (62) | 5,6 (79) |

EXAMPLES 19 TO 21 AND COMPARATIVE EXAMPLES 7 TO 9

50.0 g of the acids noted below, 400 ml anisole and 3.0 g activated carbon, Merck Art. No. 2184 were boiled under reflux in the apparatus described in example 1, and the separating water measured at predetermined time intervals. Table 7 shows the carboxylic acids used and the quantities of separated water in g and % of the theory. Comparative experiments without the use of charcoal were conducted parallel to the foregoing.

TABLE 7

| | Carboxylic acid | Activ. carbon | Separated water quantity in g and % after | | | | | | | | |
|---|---|---|---|---|---|---|---|---|---|---|---|
| | | | 1 | 2 | 3 | 4 | 5 | 7 | 8 | 9 | 10 (h) |
| Example 19 | Trimellitic acid | 3,0 g | 1,2 (28) | 2,2 (51) | 3,3 (77) | 3,8 (88) | | | | | |
| Comparative example 7 | Trimellitic acid | — | 0,0 | 0,0 | | | | | | | |
| Example 20 | Benzophenone-tetracarboxylic acid | 3,0 g | | | | | | | 4,0 (80) | | |
| Comparative | Benzophenone- | — | 0,0 | 0,0 | | | | | | | |

TABLE 7-continued

| | Carboxylic acid | Activ. carbon | Separated water quantity in g and % after | | | | | | | |
|---|---|---|---|---|---|---|---|---|---|---|
| | | | 1 | 2 | 3 | 4 | 5 | 7 | 8 | 9 10 (h) |
| example 8 | tetracarboxylic acid | | | | | | | | | |
| Example 21 | Succinic acid | 3,0 | 1,05 (14) | 1,6 (21) | 2,45 (32) | 2,95 (39) | 3,65 (48) | 4,25 (56) | 4,40 (58) | 4,80 (63) |
| Comparative example 9 | Succinic acid | — | 0,0 | 0,3 | | | | | | |

We claim:

1. Process for, respectively, the production and purification of dicarboxylic and polycarboxylic acid anhydrides by dehydration of the respective dicarboxylic or polycarboxylic acids or, in given instances, by dehydration of the respective dicarboxylic or polycarboxylic acids contained in the anhydrides to be purified, characterized by heating at temperatures from 120° to 200° C., the dicarboxylic or polycarboxylic acid, or, respectively, the anhydride to be purified, in an organic solvent in the presence of activated carbon, and by removing the water becoming free thereby in azeotropic solution with the solvent.

2. Process as per claim 1, characterized by using a solvent not miscible with water but forming an azeotrope with water, and by azeotropically distilling off, of the separated water together with the solvent.

3. Process as per claim 1, characterized by using as solvent anisole or phenetole.

4. Process as per claim 1, characterized by using pulverized activated carbon.

5. Process as per claim 1, characterized by the quantity of activated carbon amounting to a minimum of 1% by weight relative to the carboxylic acid.

* * * * *